(12) United States Patent
Kidmose et al.

(10) Patent No.: US 9,782,103 B2
(45) Date of Patent: Oct. 10, 2017

(54) PORTABLE MONITORING DEVICE WITH HEARING AID AND EEG MONITOR

(75) Inventors: Preben Kidmose, Maarslet (DK); Soren Erik Westermann, Espergarde (DK)

(73) Assignee: Widex A/S, Lynge (DK)

( * ) Notice: Subject to any disclaimer, the term of this patent is extended or adjusted under 35 U.S.C. 154(b) by 0 days.

(21) Appl. No.: 13/428,866

(22) Filed: Mar. 23, 2012

(65) Prior Publication Data

US 2012/0238856 A1 Sep. 20, 2012

Related U.S. Application Data

(63) Continuation-in-part of application No. PCT/EP2009/062764, filed on Oct. 1, 2009.

(51) Int. Cl.
*A61B 5/04* (2006.01)
*A61B 5/0484* (2006.01)
(Continued)

(52) U.S. Cl.
CPC ........ *A61B 5/04845* (2013.01); *A61B 5/0482* (2013.01); *A61B 5/16* (2013.01)

(58) Field of Classification Search
CPC ... A61B 5/0476; A61B 5/121; A61B 5/04845; A61B 5/0488; A61B 5/6817;
(Continued)

(56) References Cited

U.S. PATENT DOCUMENTS 5,999,856 A * 12/1999 Kennedy .................. 607/57
6,084,516 A 7/2000 Yasushi et al.
(Continued)

FOREIGN PATENT DOCUMENTS

EP 1073314 A1 1/2001
JP 62-89093 U 6/1987
(Continued)

OTHER PUBLICATIONS

International Search Report for PCT/EP2009/062764 dated Jun. 4, 2010.
(Continued)

*Primary Examiner* — Joseph Stoklosa
*Assistant Examiner* — Brian M Antiskay
(74) *Attorney, Agent, or Firm* — Sughrue Mion, PLLC

(57) ABSTRACT

A portable monitoring device comprises a hearing aid having a housing, a microphone (24), an acoustic signal processing means (43), and an acoustic output transducer (33). The portable monitoring device further comprises an EEG monitoring system arranged at least partly in said housing, and comprising a measuring unit (3) having electrodes (12) arranged external to the housing. The EEG monitoring system comprises a processing unit (42) for analyzing the EEG signal for identifying or predicting specific biological incidences, such as a seizure, in said person, decision means for deciding, based on said analyzed EEG signal, when an alarm or information must be provided to said person, and means for providing said alarm or information through said output transducer (33). The invention further provides a method of monitoring an EEG signal of a hearing impaired person.

23 Claims, 4 Drawing Sheets

(51) Int. Cl.
*A61B 5/0482* (2006.01)
*A61B 5/16* (2006.01)
*A61B 5/00* (2006.01)

(58) Field of Classification Search
CPC ... A61B 5/0478; A61B 5/0006; A61B 5/6814; A61B 5/6803; A61B 5/6816; A61B 5/6815; H04R 25/70; H04R 25/00; H04R 2410/00; H04R 25/02
USPC .......... 600/25, 372–373, 377, 379, 382–384, 600/386, 393, 544–545, 559; 607/115–116
See application file for complete search history.

(56) References Cited

U.S. PATENT DOCUMENTS

| | | | |
|---|---|---|---|
| 6,572,542 | B1 | 6/2003 | Houben et al. |
| 8,751,006 | B2* | 6/2014 | Saoji ................ A61N 1/36032 607/32 |
| 2004/0133371 | A1* | 7/2004 | Ziarani ........................... 702/70 |
| 2006/0235484 | A1* | 10/2006 | Jaax et al. ...................... 607/46 |
| 2007/0112277 | A1 | 5/2007 | Fischer et al. |
| 2008/0146890 | A1* | 6/2008 | LeBoeuf ............. A61B 5/0059 600/300 |
| 2008/0318640 | A1 | 12/2008 | Takano et al. |
| 2010/0324440 | A1* | 12/2010 | Moore et al. ................. 600/544 |
| 2012/0215056 | A1* | 8/2012 | Hillbratt ................ H04R 25/70 600/25 |

FOREIGN PATENT DOCUMENTS

| | | |
|---|---|---|
| JP | 11-221196 A | 8/1999 |
| JP | 2002-369294 | 12/2002 |
| JP | 2004-345477 A | 12/2004 |
| JP | 2009-5071 A | 1/2009 |
| WO | 9113584 A1 | 9/1991 |
| WO | 2006066577 A1 | 6/2006 |
| WO | 2007047667 A2 | 4/2007 |
| WO | 2007144307 A2 | 12/2007 |
| WO | 2009090110 A1 | 7/2009 |

OTHER PUBLICATIONS

Office Action for counterpart Japanese Patent Application No. 2012-530135 dated Oct. 1, 2013, with English translation.
Office Action for counterpart Japanese Patent Application No. 2012-530135 dated Mar. 4 2014 with English translation.
Office Action for counterpart Chinese Application No. 200980161783.9 dated Jan. 28, 2014 with English translation.
Communication dated May 26, 2015, issued by the Japanese Intellectual Property Office in counterpart Japanese Application No. 2014-135797.

* cited by examiner

PORTABLE MONITORING DEVICE WITH HEARING AID AND EEG MONITOR

RELATED APPLICATIONS

The present application is a continuation-in-part of application PCT/EP2009/062764, filed on Oct. 1, 2009, in Europe and published as WO 2011038767 A1.

BACKGROUND OF THE INVENTION

1. Field of the Invention

The present invention relates to portable monitoring devices. The invention further relates to portable monitoring devices comprising a hearing aid and comprising an EEG monitoring system for monitoring biological incidences. The invention more specifically relates to portable monitoring devices comprising a housing, at least one microphone for receiving ambient sound, acoustic signal processing means for processing a signal from the microphone, and an output transducer. The invention also relates to a method of monitoring an EEG signal.

In general the prevalence of hearing aid use is more profound in the population of elderly persons than in the general population.

Also the prevalence of diabetes is more profound in the elderly population, and it has been realized that there is a significant group of hearing aid users with diabetes.

For persons with diabetes, detailed control of blood sugar concentration is important. The level should not be too high in order to limit the risk of long term effects of diabetes. The blood sugar level should also not be too low, since this might lead to hypoglycemia, where the person becomes absent and may become unconscious. Hypoglycemia may be fatal. Therefore, persons with diabetes often need to measure their blood sugar level on a daily basis, or several times a day, by testing a small blood sample. Some persons with diabetes have the problem that they will not feel any warning before the blood sugar concentration has fallen to a level where hypoglycemia occurs. However, characteristic changes in the electroencephalographic (EEG) signals of a person with diabetes will be seen before the onset of hypoglycemia.

Also for persons with epilepsy, characteristic changes in the EEG signals may be seen before the onset of an attack.

2. The Prior Art

It is known from WO-A1-2006/066577 to apply a system measuring EEG signals continuously on a person, for detecting if a person with diabetes is getting close to a hypoglycemic event.

WO-A2-2007/144307 presents an algorithm for detecting hypoglycemia from an EEG signal.

In U.S. Pat. No. 6,572,542 both the EEG signal and an Electrocardiography (ECG) signal are applied for detection of hypoglycemia.

Such systems have been developed to a level where they can be carried continuously by a person without limiting the person in daily activities. If the onset of hypoglycemia is detected, e.g. according to a method described in WO-A2-2007/144307, the person is alerted by the system and is instructed to either measure the blood sugar concentration or to drink or eat something increasing the blood sugar concentration. Often a surgical operation is needed in order to arrange electrodes subcutaneously on the head. These electrodes will, in some way, be connected with an electronic device arranged on the body.

For many hearing impaired persons using a hearing aid, it may be difficult to handle this small high tech product. This may especially be a problem to elderly persons. If these persons are equipped with an EEG monitoring system, which also needs correct handling in order to function properly, the risk of incorrect handling of at least one of these two devices will most likely increase significantly. This imposes a risk of missing an alarm of an upcoming biological incidence, such as hypoglycemia, or of not having the possible optimal hearing.

Therefore, it will often be a problem to equip elderly persons with both a hearing aid and an EEG monitoring system, both being equipment to which they must pay attention and handle in specific different ways in order to obtain the benefits of these devices. Also, more devices arranged on the body of a person increase the risk of overlooking one. Further, a hearing aid user often needs two hearing aids.

SUMMARY OF THE INVENTION

The invention, in a first aspect, provides a portable monitoring device comprising a hearing aid having a housing, at least one microphone for receiving ambient sound, acoustic signal processing means for processing a signal from the microphone, and an acoustic output transducer, said portable monitoring device further comprising an EEG monitoring system for monitoring EEG signals of a person using the portable monitoring device, said EEG monitoring system being arranged at least partly in said housing, said EEG monitoring system comprising a measuring unit having electrodes for measuring one or more EEG signals from the person carrying the EEG monitor, said electrodes being arranged external to the housing or at the outer surface of the housing. Said EEG monitoring system further comprises a processing unit having EEG signal processing means for analyzing the EEG signal, said processing unit being arranged in said housing, said signal processing means being adapted for, based on the EEG signal, identifying or predicting specific biological incidences, such as a seizure, in said person, said processing unit comprising decision means for deciding, based on said analyzed EEG signal, when an alarm or information must be provided to said person, and means for providing said alarm or information through said output transducer.

A portable monitoring device comprising a hearing aid and an EEG monitoring system according to the invention will have the advantage of being only one device to remember and to handle. It can be manufactured to a smaller size and a lower price, compared to two independent devices since the housing and acoustic output transducer serve dual purposes. Also other components, such as battery and part of the electronics, may be applied for both purposes. It will be possible for the manufacturer to design the portable monitoring device comprising a hearing aid and an EEG monitoring system such that the user interface of the two can be either integrated or set up for optimal handling and control of both the hearing aid and the EEG monitoring system, thereby facilitating an overall easier handling compared to two different devices. For example the same remote control would preferably be applied for both functions.

In an embodiment the portable monitoring device comprises adjustment means for adjusting the sound level of a sound message or an alarm according to the actual acoustic background noise level in order to make the sound message clearly discernible over the background noise. This will increase the probability that the user will notice an alarm or message from the EEG monitoring system, and take action on such an alarm, thereby reducing the risk of a biological incidence. This biological incidence may be hypoglycemia. In that case, the action to be taken by the user is relatively simple, i.e. increase the blood sugar level by eating or drinking something with high glucose content.

In an embodiment of a portable monitoring device comprising a hearing aid and an EEG monitoring system, the EEG monitoring system is adapted for a wireless connection between the measuring unit and the processing unit. This facilitates a more flexible arrangement of the portable monitoring device. It will be possible to implant the measuring unit or to arrange the two units on different positions on the user's body.

In an embodiment of a portable monitoring device comprising a hearing aid and an EEG monitoring system, the measuring unit comprises an electronic module which is connected with the electrodes. This electronic module may comprise an analogue to digital converter in order to digitize the signal, making it less sensitive to noise, as close to the electrodes as possible. The electronic module is further being connected with communication means for transmitting the EEG signal to the processing unit. Such communication means may be wired, e.g. through a data bus, or wireless.

In a further embodiment of a portable monitoring device, the measuring unit of the EEG monitoring system is implanted subcutaneously on the head of the person to be monitored. This will ensure a better and more stable electrical contact between the electrodes and the tissue. Preferably the measuring unit is arranged between the scalp and the scull, thereby making the implantation relatively simple.

In a further embodiment the portable monitoring device is prepared for comprising a battery for providing power to the hearing aid and the EEG monitoring system, where the power to the measuring unit is transferred wirelessly. This makes it possible to have an implant powered from an external unit, whereby a surgical operation to change battery in an implanted measuring unit can be avoided.

In a further embodiment the measuring unit is adapted to be arranged in the ear canal with at least two electrodes adapted to be in contact with the wall of the ear canal in at least two different positions. It has been found that the ear canal is a god place for measuring EEG signals. By having the electrodes in the ear canal, implantation of the measuring unit can be avoided. Furthermore, in order for the hearing aid to function, some ear plug with means for supplying an acoustic signal to the user's eardrum will be necessary. Therefore, electrodes may be arranged with or attached to such an ear plug.

In a further embodiment the processing unit of the EEG monitoring system is adapted to be arranged behind the ear. In this embodiment the housing of the portable monitoring device is arranged behind the ear as a behind-the-ear hearing aid. This has the advantage that the housing is not directly visible, and when the measuring unit is implanted subcutaneously in an area of the head behind the ear, a good wireless contact can be obtained.

In a further embodiment the signal from the electrodes is digitized in the measuring unit before being transmitted to the EEG signal processing means in the processing unit. This can facilitate transmission through a data bus and the data can be packed for transmission. Also, the signal will be less sensitive to noise.

In a further embodiment the measuring unit and the processing unit is arranged in an ear plug casing adapted to be arranged in the ear canal, said ear plug casing being provided with an outer shape being individually matched to the shape of the ear canal. In this embodiment the electrodes will typically be arranged on the outer surface of the ear plug casing in order to be in close contact with the skin of the ear canal when mounted in an ear canal. An in-the-ear hearing aid is preferred by a number of hearing aid users, and with this embodiment it will be possible to have an in-the-ear portable monitoring device comprising an EEG monitoring system.

In a further embodiment acoustic signal processing means for the hearing aid function is placed in the housing also comprising the processing unit for the EEG monitoring system. The acoustic signal processing means is programmable in order to facilitate the adjustment of the hearing aid transfer function to the needs of the individual user. The advantage of having the two processing units in the same housing is that the wiring between them and other components arranged in the housing can be simpler. Such other components could be receiver, power supply, memory and microphone.

In a further embodiment the acoustic signal processing means and the EEG signal processing means are arranged on the same chip. This will make the wiring even simpler and may save some space facilitating a smaller housing.

In a further embodiment the acoustic signal processing means and the EEG signal processing means are programmable from an external device, such that said system can be set up to function according to needs of the individual user. Such programming could be performed by wire or wirelessly, e.g. through a relay device. A relay device can be used for wireless communication with the portable monitoring device, where a short range and low power consumption transmission is applied between the hearing aid and the relay device, whereas a longer ranging transmission is applied between the relay device and surrounding units. The programming of the portable monitoring device could be performed from one software tool programming the hearing aid parameters as well as the EEG monitoring parameters.

In a further embodiment the portable monitoring device further comprises a data logger adapted to log events in the EEG signal relevant for the identification or prediction of specific biological incidences. Such logged data may provide the user with important information which may help in avoiding future biological incidences. If an incidence is often close, but not actually occurring, on a specific time during the day, changes in the daily routines might be suggested. In the case of diabetes such changes could be to eat more, or decrease the insulin doses, before the time during the day where an incidence (here hypoglycemia) is often close. Data logging can be performed both for hearing aid related parameters and for EEG signal parameters.

In a further embodiment the portable monitoring device further comprises a radio transmitter adapted for sending information obtained from the EEG monitoring concerning a biological incidence to an external device. This will facilitate that an alarm or information could be passed directly to family members or to medical care staff. A radio receiver may also be applied for setting up the different parameters in either the hearing aid or in the EEG monitor.

In a second aspect the invention provides a method of monitoring an EEG signal of a hearing impaired person comprising the steps of providing a portable monitoring device comprising a hearing aid having a housing, at least one microphone for receiving ambient sound, acoustic signal processing means for processing a signal from the microphone, and an acoustic output transducer, said portable monitoring device further comprising an EEG monitoring system for monitoring EEG signals of a person using the portable monitoring device, said EEG monitoring system being arranged at least partly in said housing, providing a measuring unit having electrodes for measuring one or more EEG signals from the person carrying the EEG monitor, said electrodes being arranged external to the housing or at the outer surface of the housing, providing a processing unit having EEG signal processing means for analyzing the EEG signal, said processing unit being arranged in said housing, said signal processing means being adapted for, based on the EEG signal, identifying or predicting specific biological incidences, such as a seizure, in said person, said processing unit comprising decision means for deciding, based on said analyzed EEG signal, when an alarm or information must be provided to said person, said alarm or information is provided through said output transducer.

In a third aspect the invention provides a system comprising a portable monitoring device comprising a hearing aid having a housing, at least one microphone for receiving ambient sound, acoustic signal processing means for processing a signal from the microphone, and an acoustic output transducer, said portable monitoring device further comprising an EEG monitoring system for monitoring EEG signals of a person using the hearing aid, said EEG monitoring system being arranged at least partly in said housing, said EEG monitoring system comprising a measuring unit having electrodes for measuring one or more EEG signals from the person carrying the EEG monitor, said electrodes being arranged external to the housing or at the outer surface of the housing, and a processing unit having EEG signal processing means for analyzing the EEG signal, said processing unit being arranged in said housing, said signal processing means being adapted for, based on the EEG signal, identifying or predicting specific biological incidences, in said person, said processing unit comprising decision means for deciding, based on said analyzed EEG signal, when an alarm or information must be provided to said person, and means for providing said alarm or information through said output transducer said system being adapted to be arranged at one ear of a person, and further comprising a hearing aid adapted to be arranged at the other ear of the person. The hearing aid could also be substituted with a second portable monitoring device. Preferably, the first portable monitoring device and the hearing aid or second portable monitoring device can communicate wirelessly in order to provide any alarm or information to the person to both ears. This will increase the intelligibility of any messages, as binaural messages will be easier to understand.

In an embodiment of this system, it also comprises a remote control for adjusting said portable monitoring device and said hearing aid.

In a further embodiment, the system comprises a relay device. A remote control and a relay device may be combined into one unit. Such a combined unit may comprise extra memory, e.g. for data logging.

BRIEF DESCRIPTION OF THE DRAWINGS

Embodiments of the invention will now be explained in further detail with reference to the figures.

DETAILED DESCRIPTION OF THE INVENTION

Figure 1:
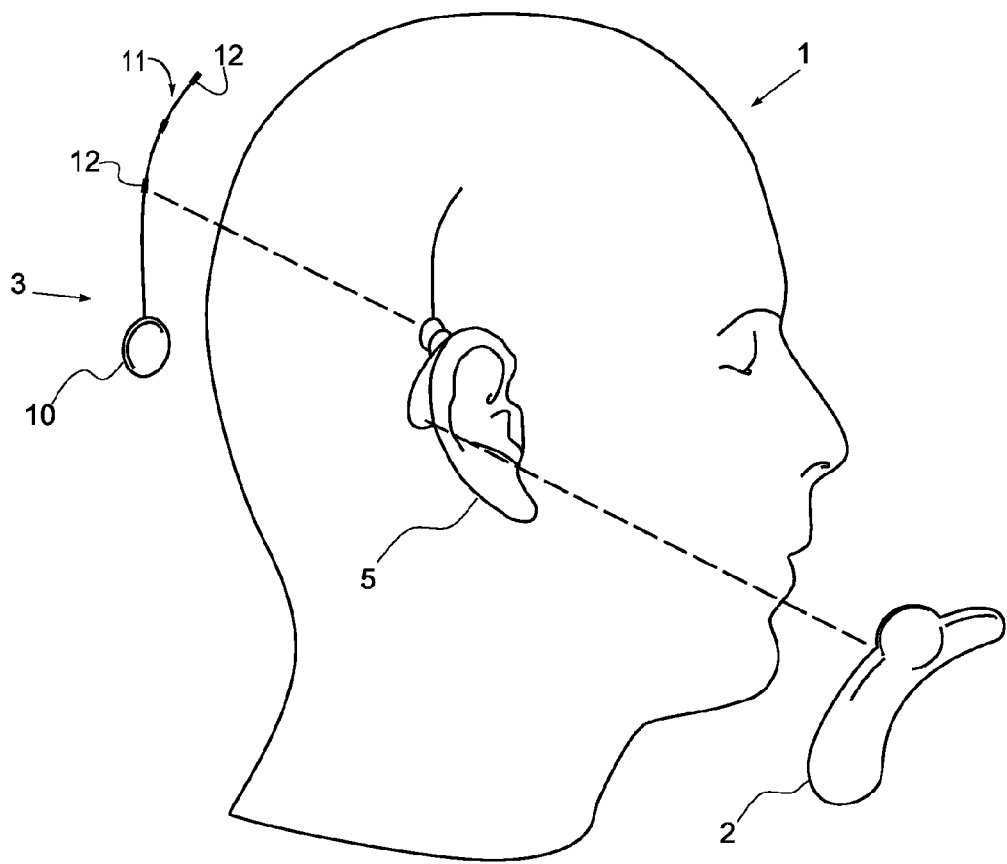
FIG. 1 illustrates an embodiment where the processing unit of the EEG monitoring system is adapted to be arranged in a behind the ear hearing aid type housing, and the measuring unit is adapted to be an implant arranged subcutaneously in the area behind the ear.

FIG. 1 shows the head 1 of a person wearing a portable monitoring device. The EEG monitoring system in FIG. 1 comprises an external unit 2, here the processing unit, and an implant unit 3, here the measuring unit. The two units 2, 3 are adapted to be in wireless communication through the skin of the person. The implanted unit 3 comprises a measuring unit having electrodes 12. The measuring unit will have at least two electrodes 12. The electrodes may be arranged as separate wires or as separate electrodes 12 in the same wire 11 as illustrated in FIG. 1. One wire comprising all electrodes may facilitate a simple implantation process. The different electrodes 12 in the wire 11 are connected independently to an electronic module 10 comprising means for converting a signal obtained by the electrodes into digital form, and further comprising means for communicating with the external unit 2.

Figure 2:
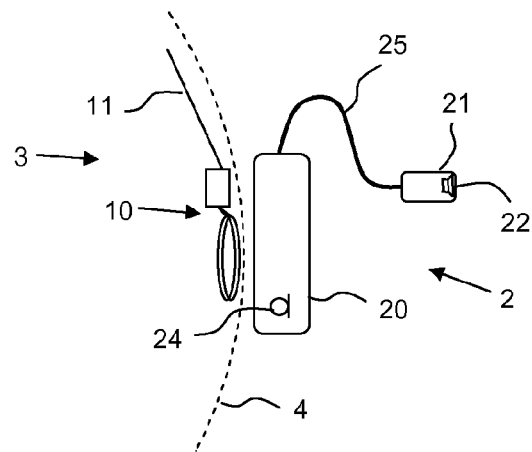
FIG. 2 illustrates the embodiment of FIG. 1 in a more schematic form.

FIG. 2 shows in schematic form the implant unit 3 arranged under the skin 4, i.e. subcutaneously, of a person, and the external unit 2 arranged right outside the skin barrier 4 of the person. In this embodiment the external unit 2 comprises a base part 20, e.g. prepared to be arranged behind the ear, and an ear canal part 21 prepared to be arranged in the ear canal of the person using the monitoring system. In a different embodiment (see FIG. 1 or 6) the external unit 2 is made up of the base part alone without an ear canal part.

The base part 20 will comprise the communication means for communicating with the implant part 3. The communication means will comprise an antenna e.g. in the form of a coil corresponding with a coil in the implant unit 3 through an inductive coupling. The base part 20 may also comprise the processing unit which is adapted for analyzing the EEG signal in order to identify or predict any biological incidence which may be found from an analysis of the EEG signal. The base part 20 will typically also comprise the power supply in the form of a battery. Also, the base part will often comprise one or two microphones for the hearing aid function, which may also be applied for measuring the background noise level. This noise level can be applied as input for processing means set up for adjusting the sound level of a sound message according to the actual acoustic background noise level. In general, sound messages may also be related to the hearing aid function and to information related to the EEG monitoring system other than alarms directed to the onset of hypoglycemia.

The ear canal part 21 may be formed as an ear plug comprising means for supplying an acoustic signal to the person carrying the monitoring system. Such means for supplying an acoustic signal may be a receiver or loudspeaker 22 arranged in the ear canal part 21 and provided with an electrical signal through a wire from signal processing means in the base part 20. The means for supplying an acoustic signal may also be a sound tube arranged in the ear canal part 21 in one end, and in the base part 20 in the other end. A receiver or loudspeaker 22 is then arranged in the base part 20 supplying the acoustic signal to the sound tube, where the sound tube is guiding the acoustic signal to the ear canal part 21. The means for supplying an acoustic signal is applied for both the amplified hearing aid signal as well as for any alarm or information from the EEG monitoring system. An ear canal part formed as an ear plug is preferably shaped to the form of the user's ear canal.

The implant unit 3 also shown in FIG. 2 comprises electrodes 12 and an electronic module 10. The electronic module comprises an antenna for communication with the base part 20 of the external unit 2. This antenna may be in the form of a coil for inductive coupling. But also other types of antennas may be applied. The electronic module 10 also comprises analogue to digital conversion means and e.g. means for controlling the signal transfer to the base part 20.

The implant unit 3 also comprises power supply means for the electronic module. This may be in the form of a battery which can be recharged by external means, e.g. through induction, or which is recharged from a system generating power from e.g. heat differentials in the body or from kinetic energy generated from body movement. The implant unit 3 may also be continuously powered through an inductive coupling from the base part of the external unit 2.

Figure 3:
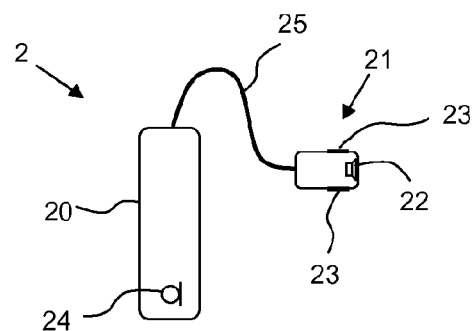
FIG. 3 illustrates an embodiment with the measuring unit adapted to be arranged in the ear canal.

FIG. 3 shows an embodiment where the measuring unit is arranged in the ear canal part 21. In this embodiment the electrodes 23 for detecting the EEG signal are arranged on the outside surface of the ear canal part, where they will be in contact with the skin in the ear canal when the ear canal part is in use. Preferably, the ear canal part 21 is formed into an ear plug fitting the specific ear canal of the portable monitoring device user. Thereby, the electrodes can be easily arranged in the same position whenever the ear canal part is arranged in the ear canal. This may be important in order to avoid that changes in the EEG signal could be caused by a change in the position of the electrodes 23.

Figure 4:
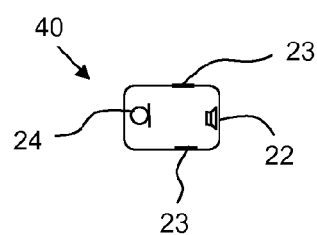
FIG. 4 illustrates an embodiment with both the processing unit and the measuring unit adapted to be arranged in the ear canal.

FIG. 4 shows an embodiment where all parts of the portable monitoring device are prepared to be arranged in the ear canal. This embodiment will be formed as a so-called in-the-ear hearing aid comprising a hearing aid and an EEG monitoring system. The portable monitoring device according to this embodiment will preferably be formed into an ear plug, fitting the ear of the hearing aid user.

Figure 5:
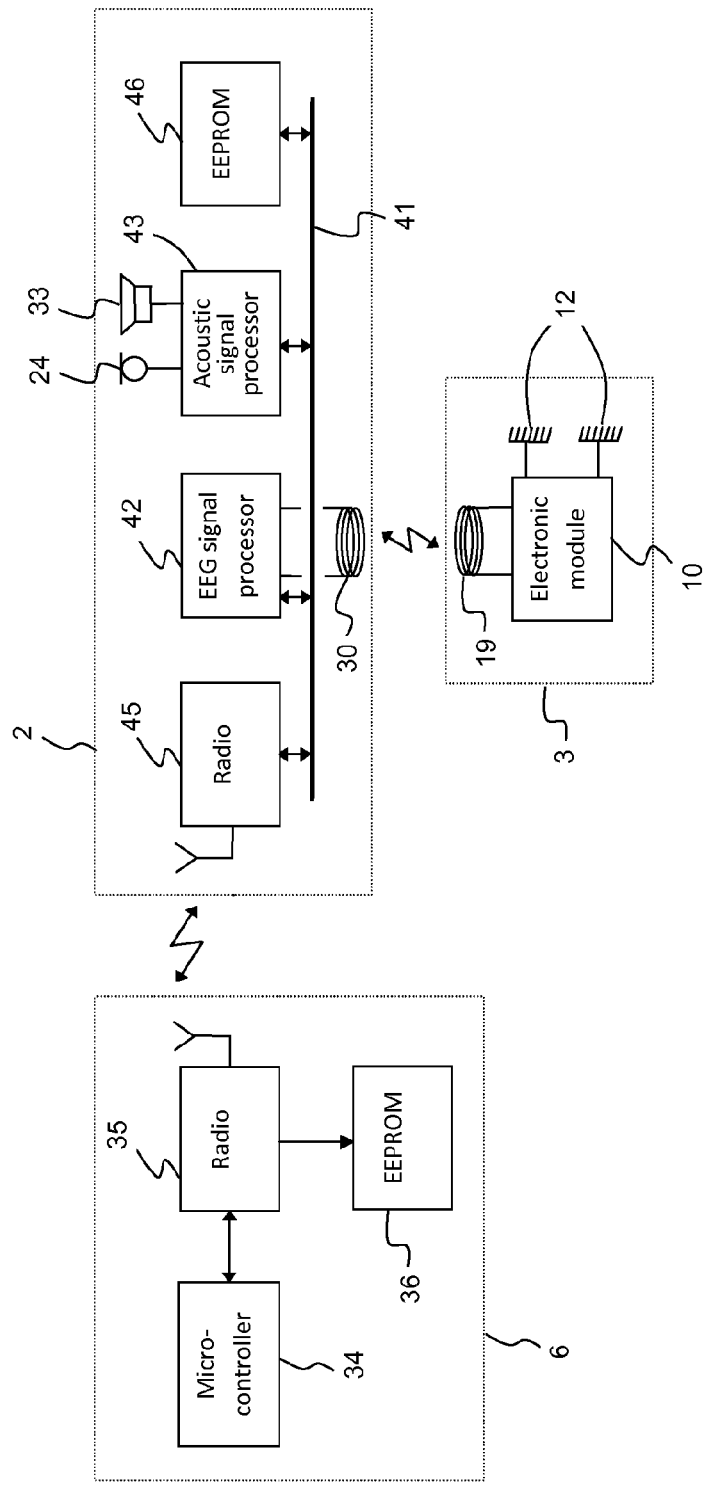
FIG. 5 illustrates an example of functional elements in an embodiment of FIG. 1.

FIG. 5 shows the main components of a portable monitoring device according to an embodiment of FIG. 1 or 2, which is set up for communication with an external unit 6 such as a remote control or a relay device for assisting the portable monitoring device in wireless communication between the portable monitoring device and the surroundings. The portable monitoring device is arranged in a housing 2 comprising the acoustic signal processing means 43 and the EEG signal processing means 42. The measuring unit 3 for the EEG monitoring system is arranged external to the housing 2 and is prepared for wireless communication with the EEG signal processor 42. The wireless communication between the measuring unit 3 and the EEG signal processor 42 may be performed through inductive coils 19, 30, which also allow for wireless transfer of power to the measuring unit 3. This is particularly advantageous when the measuring unit 3 is implanted.

The EEG signals are to be measured by electrodes 12 arranged subcutaneously with the measuring unit 3. The analogue EEG signals are digitized and packed for sending by the electronic module 10. When the EEG signals have been transferred to the EEG signal processor the signals are analyzed in order to detect any changes in the signals over time which may indicate onset of hypoglycemia. If the signal analysis indicate that onset of hypoglycemia may be approaching, a message is sent to the acoustic signal processor from where an acoustic alarm or information is provided through an acoustic output transducer 33, i.e. a receiver or loudspeaker. A microphone 24 is applied for measuring the surrounding sound pressure level, and the output of the receiver 33 is thus adjusted to this background noise. Individual settings for the EEG monitoring system may be stored in the memory EEPROM 46 in the portable monitoring device, and such settings can be accessed through the internal bus 41 connecting the different components in the portable monitoring device housing 2. Individual settings for the EEG monitoring system may comprise parameters setting up the EEG signal processor for identifying or predicting the specific biological incidence relevant for the user. This could be hypoglycemia or epileptic attacks. In the case of hypoglycemia, parameters could also be specifying how early an alarm of hypoglycemia should be given. This is relevant since the onset of hypoglycemia may have different causes for different individuals.

The internal memory of the portable monitoring device 46, which in this example is an EEPROM, will also be applied for storage of the hearing aid parameters such as data representing the audiogram of the hearing aid user as well as other parameters set up for the individual user. These parameters are stored in the portable monitoring device memory 46 during the fitting of the hearing aid part. This is done by transferring the parameters from the hearing aid fitter's computer through a wired connection, or wirelessly as illustrated in FIG. 5, to the portable monitoring device memory.

The wireless connection between the portable monitoring device and an external unit is preferably based on a low power consumption radio 45 receiver and transmitter communicating with a radio 35 in e.g. a relay device 6. The relay device is also referred to as a DEX unit within hearing aid technology (Available from Widex A/S, Lynge, Denmark). The external unit with a radio 35 could also be the computer of the fitter. A relay device 6 or DEX may be applied for a number of other purposes than transferring set-up parameters for the portable monitoring device. The relay device 6 is often arranged to be carried on the breast in a line or lanyard around the neck of a hearing aid user. It may be in wireless communication with other units, where a communication standard with higher power demands, such as Bluetooth (Trademark), can be applied because the relay device is usually larger and equipped with substantially larger, and therefore more powerful, batteries than possible in e.g. hearing aids.

A relay device 6 may be applied for streaming sound to the portable monitoring device. This could be sound from a television or from a microphone external to the portable monitoring device. The relay device 6 may further be supplied with further memory capacity, such as a flash memory, which could be applied for storage of data logged by the portable monitoring device or for storage of sound files to be streamed to the portable monitoring device. Such logged data could be statistical data comprising information on sound environment and on the EEG signal. Such data could be stored continuously in the EEPROM 46, and transferred to a flash memory, e.g. in a relay device, when necessary.

Figure 6:
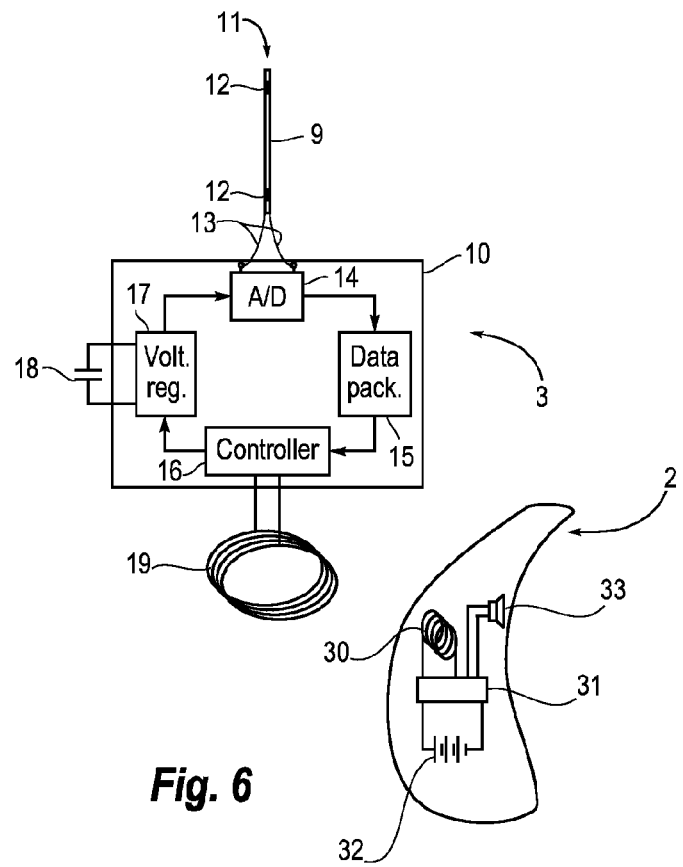
FIG. 6 illustrates an embodiment with an implantable measuring unit and a housing.

FIG. 6 shows a portable monitoring device comprising a hearing aid and an EEG monitoring system according to the embodiment of FIG. 1 in more details. Focus in FIG. 6 is on the EEG monitoring system. The implant unit 3 is suitable for being subcutaneously positioned behind the ear of a person to be EEG monitored. The implant unit 3 comprises a subcutaneous electrode wire 11 having a plurality of active areas 12 separated by isolators 9, said electrode wire 11 being connected to an electronic circuit 10. The EEG electrode wire 11 shown in this embodiment has two active areas 12, each individually connected and arranged to be individual electrodes, but other embodiments may require an EEG electrode having three or more active areas. The electronic circuit 10 comprises an A/D converter 14, a data packet controller 15, a communications controller 16, and a voltage regulator 17. Preferably, the A/D converter 14 is of a low power consumption type. The electrode wire 11 is connected to the input terminals of the A/D converter 14 via electrode wires 13, the communications controller 16 is connected to a first communication coil 19, and the voltage regulator 17 is connected to a ceramic capacitor 18. The ceramic capacitor 18 as well as the communication coil 19 are both arranged as part of the implant unit 3.

The external part 2 of the EEG monitoring system in FIG. 6 comprises a controller 31 connected to a second communications coil 30, a battery 32 for powering the controller 31, and a receiver (i.e. loudspeaker) 22 for providing an acoustic signal, e.g. a sound message in the event of a biological incidence, such as a seizure, is coming up. The controller 31 comprises the EEG signal processor and the acoustic signal processor. The external part 2 also comprises at least one microphone (not shown). In addition to being applied for the hearing aid function a microphone can be applied for measuring background noise in order to adjust the sound pressure level of a sound message according to the background noise level.

When in use, the external unit 2 of the EEG monitoring system may be placed behind the ear of a user for whom monitoring of an EEG signal is desired, and in the vicinity of the subcutaneously implanted unit 3, which is to be implanted right below the skin and slightly behind the ear of the user and positioned in such a way that a reliable, electrical EEG signal may be detected by the electrode wire 11.

The electrode wire 11 picks up EEG signals as a varying electrical voltage potential between two of the active areas 12 and feeds the varying electrical voltage to the input terminals of the A/D converter 14 via the electrode wires 13. The A/D converter 14 converts the varying electrical voltage from the electrode wire 11 into a digital signal and presents said digital signal to the data packet controller 15. The data packet controller 15 arranges the digital signal representing the electrical signal from the electrode wire 11 into a stream of data packets according to a predetermined communications protocol, and feeds the resulting stream of data packets to the communications controller 16.

The communications controller 16 is configured to two operational purposes. The first purpose of the communications controller 16 is to enable the electronic circuit 10 to be energized electromagnetically by receiving energy from the second communications coil 30 of the external part 2 by the first communications coil 19. The electromagnetic energy received in the first communications coil 19 is transferred by the communications controller 16 to the voltage regulator 17 and stored briefly as a charge in the ceramic capacitor 18. The electrical energy stored in the ceramic capacitor 18 is then used as a power source for the electrical circuit 10.

The second purpose of the communications controller 16 is to take data packets, representing the electrical EEG signals from the electrode wire 11, from the data packet controller 15 and convert them in the first communications coil 19 into bursts of electromagnetic energy suitable for being received and detected by the second communications coil 30 of the external part 2. The second communications coil 30 converts the received electromagnetic energy into an electrical signal suitable for being continuously decoded and analyzed by the controller 31.

Depending on the results of the analysis of the EEG signals, decisions may be taken by the controller 31 to activate the receiver 22 sounding an alarm or providing information, e.g. when a predetermined medical condition is deemed to be present from the analysis of the EEG signals. This alarm may then alert a user to the medical condition, and allow him or her to take adequate steps to alleviate the medical condition, e.g. by taking a prescription drug or consulting medical personnel to ask for immediate advice or help, depending on the medical condition.

Figure 7:
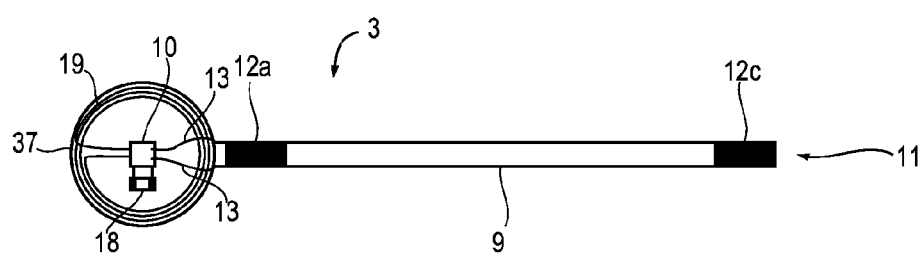
FIG. 7 illustrates an implantable measuring unit in a top view.
Figure 8:
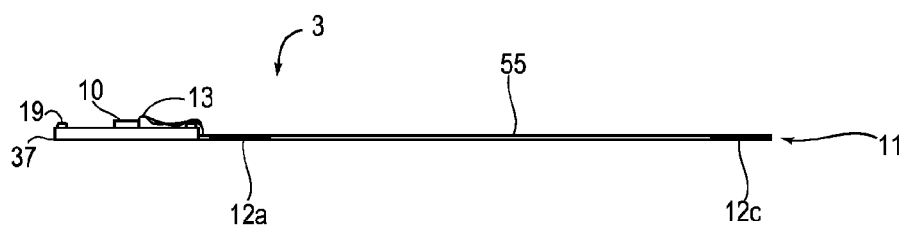
FIG. 8 illustrates the implantable measuring unit of FIG. 7 in a side view.

FIGS. 7 and 8 show an embodiment of the implantable unit 3 shown in FIG. 6. FIG. 7 shows a top view of the implantable unit 3, and FIG. 8 shows a corresponding side view of the implantable unit 3. The implantable unit 3 comprises an electrode wire 11 having isolated areas 9, active areas 12a, 12c for contacting subcutaneous tissue in order to detect the presence of an electrical signal, and a substantially circular carrier element 37 comprising an electronic circuit 10, a ceramic capacitor 19, and a first communication coil 19. The implantable unit 3 is configured for subcutaneous implantation behind the ear of a user. The electrode wire 11 is embodied as an elongated member, which as an example has a physical length of about 60 mm and a physical width of approximately 1 mm, and the substantially circular carrier element 37 has a diameter of e.g. approximately 20 mm in order to make the implant unit 3 easily implantable.

The implant unit 3 with the electrode wire 11 is arranged to be implanted subcutaneously behind the ear of a user in order to provide a signal suitable for detection by the electronics of the EEG monitoring system. A typical output signal from the EEG electrode has a magnitude in the range of approximately 1 µV to 100 mV. Muscular contractions usually generate voltage levels of a magnitude of 10 mV, but such signals are filtered out by the system. The intrinsic noise level of the electrode is about 1 µV RMS measured over a bandwidth from 0.1 to 100 Hz, and the useable bandwidth of the output signal is 0.1 to 40 Hz. The electrode has a bio-compatible PTFE polymer base, and the electrode contacts are made from a, likewise bio-compatible, platinum-iridium-alloy [Pt—Ir] with 90% platinum and 10% iridium.

Prior to implantation, the implantable unit 3 is encased completely in a bio-compatible resin (not shown), except the electrode wire 11, in order to protect the electronic circuitry from the environment of the surrounding tissue posterior to implantation. When the external unit 2 is worn behind the ear where the implant has been positioned, the second communications coil 30 of the external part will be less than one cm from the first communications coil 19 of the implantable unit 3, thus facilitating communication between the implantable unit 3 and the external unit 2 of the EEG monitoring system. This communication includes the external unit 2 delivering electromagnetic energy to the implantable unit 3, and the implantable unit 3 transmitting data representing signals from the electrode wire 11 to the external unit 2 for analysis.

In general, several components may be applied for hearing aid functions as well as for EEG monitoring functions.

Further to a receiver, this applies to a microphone, power supply and to signal processing means for the two functions. Signal processing means necessary for the two different functions may be integrated on the same electronic chip. In the embodiment of the EEG monitoring system comprising an external unit 2 and an implant unit adapted to be in wireless communication, the antenna of the external unit may be adapted for wireless communication with peripheral devices, such as devices for streaming audio to the hearing aid or devices for receiving an alarm from the EEG monitoring system.

In the case where a person needs two hearing aids, only one of these may need to be combined with an EEG monitor into a portable monitoring device. Anyway, an alarm or information from the EEG monitoring system may be supplied through both hearing aids in order to improve the audibility. The portable monitoring device and the hearing aid may be wirelessly connected in order to achieve this. The audibility may be further improved by improving the binaural masking level by phase shifting the signal to one of the hearing aids by 180 degrees.

It will also be advantageous to reduce the level of amplification of the sound from the microphone of the hearing aid in the portable monitoring device, and e.g. in the further hearing aid, during any alarm or information from the EEG monitoring system. The level of amplification should be reduced to a level where the sound pressure level in front of the eardrum caused by the amplified sound from the surroundings will not reduce the intelligibility or perception of any alarm or message from the EEG monitoring system. The reduction in amplification could further be decided from the importance or urgency of the alarm or message from the EEG monitoring system.

In most embodiments both the hearing aid part and the EEG monitoring system of the portable monitoring device will comprise programmable parts or parameters adapting the hearing aid function as well as the EEG monitor function to the individual user. Such programming could be performed from the same software platform even though the two sets of parameters may need to be decided on by two different specialists, i.e. one for the hearing aid functions and one for the EEG monitoring. The programming could be performed through a wired connection or wirelessly, e.g. via a relay device. Programming or adjustment of the initial programming could also be performed over the internet.

If the portable monitoring device comprises a data logger, this can preferably be set up for logging hearing aid related data as well as EEG related data. The hearing aid related data to be logged could be data describing the sound environment in which the hearing aid has been applied and user selected programs of the hearing aid in corresponding sound environments. EEG related data could be number of and time of alarms and events where an alarm was close but prevented before the alarm was given. Also a logging of the specific time when e.g. the blood sugar level seems to be low could be of relevance.

Most portable monitoring device users will have the need of removing and switching off their hearing aids when going to sleep. However, it is often preferable also to have the EEG monitoring during sleep. Therefore, it should be possible to switch off the hearing aid function without switching off the EEG monitoring function. A remote control could be applied for this purpose.

We claim:

1. A portable monitoring device comprising:
   a hearing aid having a hearing aid housing, at least one microphone for receiving ambient sound, an acoustic signal processor configured to process a signal from the microphone in accordance with a hearing impairment of a person using said hearing aid to obtain a processed sound signal, and an acoustic output transducer configured to produce an acoustic output corresponding to the processed sound signal, and
   an EEG monitoring system configured to monitor EEG signals of said person, said EEG monitoring system being arranged at least partly in said hearing aid housing, said EEG monitoring system comprising
      a measuring unit having electrodes for measuring one or more EEG signals from said person, said electrodes being arranged external to the housing or at an outer surface of the housing,
      a processing unit having an EEG signal processor configured to analyze the EEG signal, said processing unit being arranged in said housing, said EEG signal processor being adapted for, based on the EEG signal, identifying or predicting specific biological incidences, in said person, said processing unit comprising a decision component for deciding, based on said analyzed EEG signal, when an alarm or information must be provided to said person, and a notification component for providing said alarm or information through said output transducer; and
      an adjustment component receiving a signal representing an acoustic background noise level and configured to adjust a sound level of said alarm or information according to the acoustic background noise level in order to make the alarm or information clearly discernible over background noise.

2. The monitoring device according to claim 1, wherein said adjustment component comprises said acoustic signal processor.

3. The monitoring device according to claim 1, wherein said biological incidence is hypoglycemia.

4. The monitoring device according to claim 1, wherein said EEG monitoring system is adapted for a wireless connection between the measuring unit and the processing unit.

5. The monitoring device according to claim 4, wherein said measuring unit comprises an electronic module, said electronic module being connected with the electrodes, and further being connected with a communication component for transmitting the EEG signal to the processing unit.

6. The monitoring device according to claim 5, wherein said measuring unit is implanted subcutaneously on a head of the person to be monitored.

7. The monitoring device according to claim 1, comprising a battery for providing power to the hearing aid and to the EEG monitor, where the power to the measuring unit of the EEG monitor is transferred wirelessly.

8. The monitoring device according to claim 1, wherein said measuring unit is adapted to be arranged in an ear canal with at least two electrodes adapted to be in contact with a wall of the ear canal in at least two different positions.

9. The monitoring device according to claim 8, wherein the processing unit is adapted to be arranged behind an ear.

10. The monitoring device according to claim 9, wherein the signal from the electrodes is digitized in the measuring unit before being transmitted to the EEG signal processor in the processing unit.

11. The monitoring device according to claim 8, wherein the measuring unit and the processing unit are arranged in an ear plug casing adapted to be arranged in the ear canal, said ear plug casing being provided with an outer shape being individually matched to a shape of the ear canal.

12. The monitoring device according to claim 1, wherein said acoustic signal processor is programmable in order to facilitate adjustment of a hearing aid transfer function to needs of an individual user.

13. The monitoring device according to claim 1, wherein the acoustic signal processor and the EEG signal processor are arranged on a common chip.

14. The monitoring device according to claim 13, wherein the acoustic signal processor and the EEG signal processor are programmable from an external device, such that said portable monitoring device can be set up to function according to needs of an individual user.

15. The monitoring device according to claim 1, comprising a data logger adapted to log events in the EEG signal relevant for identification or prediction of specific biological incidences.

16. The monitoring device according to claim 1, comprising a radio transmitter adapted for sending information obtained from the EEG monitoring concerning a biological incidence to an external device.

17. A method of monitoring an EEG signal of a hearing impaired person comprising the steps of
providing a hearing aid having a housing, at least one microphone for receiving ambient sound, an acoustic signal processor configured to process a signal from the microphone in accordance with a hearing impairment of said person to obtain a processed sound signal, and an acoustic output transducer configured to produce an acoustic output corresponding to said processed sound signal, and
providing an EEG monitoring system for monitoring EEG signals of said person, said EEG monitoring system being arranged at least partly in said housing, wherein said step of providing said EEG monitoring system comprises the steps of:
providing a measuring unit having electrodes for measuring one or more EEG signals from said person, said electrodes being arranged external to the housing or at an outer surface of the housing, and
providing a processing unit having an EEG signal processor for analyzing the EEG signal, said processing unit being arranged in said housing, said EEG signal processor being adapted for, based on the EEG signal, identifying or predicting specific biological incidences, such as a seizure, in said person, said processing unit comprising a decision component for deciding, based on said analyzed EEG signal, when an alarm or information must be provided to said person, a notification component for providing said alarm or information through said output transducer; and an adjustment component receiving a signal representing acoustic background noise level and configured to adjust a sound level of said alarm or information according to the acoustic background noise level in order to make the sound or information clearly discernible over background noise.

18. A system comprising a portable monitoring device comprising a hearing aid having a housing, at least one microphone for receiving ambient sound, an acoustic signal processor configured to process a signal from the microphone in accordance with a hearing impairment of a person using said hearing aid to obtain a processed sound signal, and an acoustic output transducer configured to produce an acoustic output corresponding to said processed sound signal, said portable monitoring device further comprising an EEG monitoring system for monitoring EEG signals of said person, said EEG monitoring system being arranged at least partly in said housing, said EEG monitoring system comprising
a measuring unit having electrodes for measuring one or more EEG signals from said person, said electrodes being arranged external to the housing or at an outer surface of the housing,
a processing unit having an EEG signal processor for analyzing the EEG signal, said processing unit being arranged in said housing, said EEG signal processor being adapted for, based on the EEG signal, identifying or predicting specific biological incidences, in said person, said processing unit comprising a decision component for deciding, based on said analyzed EEG signal, when an alarm or information must be provided to said person, and a notification component for providing said alarm or information through said output transducer, said system being adapted to be arranged at one ear of a person, and further comprising a hearing aid adapted to be arranged at the other ear of the person; and
an adjustment component receiving a signal representing acoustic background noise level and configured for adjusting a sound level of said alarm or information according to the acoustic background noise level in order to make the alarm or information clearly discernible over background noise.

19. The system according to claim 18, comprising a remote control for adjusting said portable monitoring device and said hearing aid.

20. The system according to claim 18, comprising a relay device.

21. The device according to claim 1, further comprising an internal bus to which said acoustic signal processor, said EEG signal processor and a memory are connected in common, the parameters used for acoustic signal processing in said acoustic signal processor and the parameters used for EEG signal processing in said EEG signal processor are both stored in the memory connected to the internal bus.

22. The system according to claim 17, wherein said adjustment component employs a processing function provided by said acoustic signal processor.

23. The system according to claim 18, wherein said adjustment component employs a processing function provided by said acoustic signal processor.

* * * * *